(12) United States Patent
Mandecki (10) Patent No.: US 6,686,158 B2
(45) Date of Patent: Feb. 3, 2004

(54) ELECTRONICALLY-INDEXED SOLID-PHASE ASSAY FOR BIOMOLECULES

(75) Inventor: Wlodek Mandecki, Libertyville, IL (US)

(73) Assignee: Pharma Seq, Inc., Monmouth Junction, NJ (US)

( * ) Notice: Subject to any disclaimer, the term of this patent is extended or adjusted under 35 U.S.C. 154(b) by 363 days.

(21) Appl. No.: 09/908,317

(22) Filed: Jul. 17, 2001

(65) Prior Publication Data

US 2002/0006673 A1 Jan. 17, 2002

Related U.S. Application Data (63) Continuation of application No. 09/163,823, filed on Sep. 30, 1998, now abandoned, which is a continuation of application No. 08/880,489, filed on Jun. 23, 1997, now abandoned, which is a continuation of application No. 08/565,007, filed on Nov. 30, 1995, now Pat. No. 5,641,634.

(51) Int. Cl.[7] .............................................. G01N 33/543
(52) U.S. Cl. ................ 435/6; 340/825.54; 340/825.06; 340/870.11; 422/55; 422/57; 422/82.05; 435/7.1; 435/810; 435/973; 435/975; 436/518; 436/519; 436/520; 436/522; 436/523; 436/527; 436/533; 436/535; 436/172
(58) Field of Search ................... 435/7.1, 7.92, 7.93, 7.94, 810, 973, 975, 6; 436/519, 520, 522, 518, 523, 527, 533, 535, 172; 340/825.54, 825.06, 870.11; 422/55, 57, 82.05

(56) References Cited

U.S. PATENT DOCUMENTS

| | | |
|---|---|---|
| 4,177,253 A | 12/1979 | Davies et al. |
| 4,297,337 A | 10/1981 | Mansfield et al. |
| 4,452,773 A | 6/1984 | Molday |
| 4,454,234 A | 6/1984 | Czerlinski |
| 4,556,883 A | 12/1985 | Strietzel |
| 4,672,040 A | 6/1987 | Josephson |
| 4,777,145 A | 10/1988 | Luotola et al. |
| 4,778,769 A | 10/1988 | Forrest et al. |
| 4,822,566 A | 4/1989 | Newman |
| 4,857,893 A | 8/1989 | Carroll |
| 4,923,819 A | 5/1990 | Fernandez et al. |
| 4,941,201 A | 7/1990 | Davis |
| 4,965,188 A | 10/1990 | Mullis et al. |

(List continued on next page.)

FOREIGN PATENT DOCUMENTS

| | | |
|---|---|---|
| EP | 0526173 A2 | 2/1993 |
| WO | WO90/13666 | 11/1990 |
| WO | WO93/04199 | 3/1993 |

(List continued on next page.)

OTHER PUBLICATIONS

Albretsen, C et al. "Applications of magnetic beads with covalently attached oligonucleotides in hybridization: Isolation and detection of specific measles virus nRNA from a crude cell lysate" *Analytical Biochemistry* (1990) vol. 189, pp. 40–50.

Alper, J. "Drug Discovery on the assembly line" *Science* (Jun. 3, 1994) vol. 264, pp. 1399–1401.

(List continued on next page.)

*Primary Examiner*—Christopher L. Chin
(74) *Attorney, Agent, or Firm*—Morgan, Lewis & Bockius LLP (57) ABSTRACT

Disclosed are materials and methods for detecting biomolecules in samples employing transponders associated with the bead(s) used as the solid phase in the assay, and information pertinent to the assay is encoded on the transponders memory elements. A dedicated read/write device is used remotely to encode or remotely to read the information. The invention can be used in direct or competitive ELISA-type assays, or in multiplex assays for the simultaneous assay of several analytes.

10 Claims, 8 Drawing Sheets

U.S. PATENT DOCUMENTS

| | | | |
|---|---|---|---|
| 5,019,815 A | 5/1991 | Lemelson et al. | |
| 5,034,192 A | 7/1991 | Wrighton et al. | |
| 5,071,774 A | 12/1991 | Vorpahl et al. | |
| 5,153,583 A | 10/1992 | Murdoch | |
| 5,200,051 A | 4/1993 | Cozzette et al. | |
| 5,202,231 A | 4/1993 | Drmanac et al. | |
| 5,214,409 A | 5/1993 | Beigel | |
| 5,218,343 A | 6/1993 | Stobbe et al. | |
| 5,223,851 A | 6/1993 | Hadden et al. | |
| 5,235,326 A | 8/1993 | Beigel et al. | |
| 5,245,332 A | 9/1993 | Katzenstein | |
| 5,250,944 A | 10/1993 | Urbas et al. | |
| 5,252,962 A | 10/1993 | Urbas et al. | |
| 5,257,011 A | 10/1993 | Beigel | |
| 5,262,772 A | 11/1993 | Urbas et al. | |
| 5,266,926 A | 11/1993 | Beigel | |
| 5,284,748 A | 2/1994 | Mroczkowski et al. | |
| 5,347,263 A | 9/1994 | Carroll et al. | |
| 5,422,636 A | 6/1995 | Urbas et al. | |
| 5,440,300 A | 8/1995 | Spillman, Jr. | |
| 5,445,970 A | 8/1995 | Rohr | |
| 5,466,348 A | 11/1995 | Holm-Kennedy | |
| 5,481,262 A | 1/1996 | Urbas et al. | |
| 5,491,097 A | 2/1996 | Ribi et al. | |
| 5,492,806 A | 2/1996 | Drmanac et al. | |
| 5,525,464 A | 6/1996 | Drmanac et al. | |
| 5,552,270 A | 9/1996 | Khrapko et al. | |
| 5,641,634 A | 6/1997 | Mandecki | |
| 5,736,332 A | 4/1998 | Mandecki | |
| 5,741,462 A | 4/1998 | Nova et al. | |
| 5,751,629 A | 5/1998 | Nova et al. | |
| 5,770,455 A | 6/1998 | Cargill et al. | |
| 5,874,214 A | 2/1999 | Nova et al. | |
| 5,925,562 A | 7/1999 | Nova et al. | |
| 5,961,923 A | 10/1999 | Nova et al. | |
| 5,972,639 A | 10/1999 | Parandoosh | |
| 5,981,166 A * | 11/1999 | Mandecki | 435/4 |
| 6,001,571 A * | 12/1999 | Mandecki | 435/6 |
| 6,017,496 A | 1/2000 | Nova et al. | |
| 6,025,129 A | 2/2000 | Nova et al. | |
| 6,046,003 A * | 4/2000 | Mandecki | 435/6 |
| 6,051,377 A * | 4/2000 | Mandecki | 435/6 |
| 6,361,950 B1 * | 3/2002 | Mandecki | 435/6 |
| 6,376,187 B1 * | 4/2002 | Mandecki | 435/6 |
| 6,387,623 B1 * | 5/2002 | Mandecki | 435/6 |

FOREIGN PATENT DOCUMENTS

| | | |
|---|---|---|
| WO | WO93/21340 | 10/1993 |
| WO | WO96/36436 | 11/1996 |
| WO | WO97/19958 | 6/1997 |
| WO | WO97/20073 | 6/1997 |
| WO | WO97/20074 | 6/1997 |

OTHER PUBLICATIONS

Atkinson, T et al. "A convenient procedure for the synthesis of oligodeoxyribonucleotide affinity columns for the isolation of mRNA" *Nucleic Acids Research*, (1988), vol. 16, No. 13.

Cargill, JF and BE Toyonaga. *The Chemical Factory: An Assembly Line Approach to Automated Combinatorial Chemistry on Solid Phase.*

Caruthers, MH et al. "Deoxyoligonucleotide synthesis via the phosphoramidite method" *Gene Amplification and Analysis*, vol. III, (TS Papas et al., eds.) Elsevier Press, Amsterdam.

Drmanac, R et al., "DNA sequence determination by hybridization: a strategy for efficient large–scale sequencing." *Science* (1993) vol. 260, pp. 1649–1652.

Flore, F et al. "The Abbott IMx Automated Benchtop Immunochemistry Analyzer System" *Clinical Chemistry* (1998) vol. 34, No. 9.

Ghosh, SS and GF Musso. "Covalent attachment of oligonucleotides to solid supports" *Nucleic Acids Research*, (1987) vol. 15, No. 13.

Gingeras TR et al. "Hybridization properties of immobilized nucleic acids" *Nucleic Acids Research* (1987) vol. 15, No. 13.

Hooft van Hujisduijnen, RAM et al. "A means to reduce the complexity of oligonucleotides encoding degenerate peptides" *Nucleic Acids Research* (1992) vol. 20, No. 4.

Hultman et al. "Direct solid phase sequencing of genomic DNA using magnetic beads as solid support" *Nucleic Acids Research* (1989) vol. 17, No. 13, pp. 4937–4946.

Ihalainen et al. *Biotechniques* (1994) vol. 16, pp. 938–943.

Kurstak, E. *Enzyme Immunodiagnostics* (1986) pp. 13–22, Academic Press, NY.

Lam, KS et al. "A new type of synthetic peptide library for identifying ligand–binding activity" *Nature* (Nov. 7, 1991) vol. 354, pp. 82–84.

Maskos, E. et al. "Oligonucleotide hybridisations [sic] on glass supports: a novel linker for oligonucleotide synthesis and hybridisation [sic] properties of oligonucleotides synthesized *in situ*" *Nucleic Acids Research* (1992) vol. 20, No. 7, pp. 1679–1684.

McHugh, T. "Flow Microsphere Immunoassay for the Quantitative and Simultaneous Detection of Multiple Soluble Analytes" *Methods in Cell Biology* (1990) vol. 42, pp. 575–595.

Mirzabekov, AD. "DNA sequencing by hybridization—a megasequencing method and a diagnostic tool" *Tibtech* (1994) vol. 12.

Moran et al. "Radio frequency tag encoded combinatorial library method for the discovery of tripeptide–substituted cinnamic acid inhibitors of the protein tyrosine phosphatase PTP1B" *J. Am. Chem. Soc.* (1995) vol. 117, pp. 10787–10788.

Morrissey, NE et al. "Modified method for determining carcinoembryonic antigen in the presence of human anti–murine antibodies" *Clinical Chemistry* (1993) vol. 39, No. 3.

Nicolaou et al. "Radiofrequency encoded combinatorial chemistry" *Angew. Chem Int. Ed.* (1995), vol. 34, No. 210, pp. 2289–2291.

Pease, AC et al. "Light–generated oligonucleotide arrays for rapid DNA sequence analysis" *Proc. Natl. Acad. Sci.* (1994), vol. 91, pp. 5022–5026.

Pierce catalog. (1994) pp. T159, T314–T315, Rockford, Illinois US.

*Principles And Practice Of Immunoassay*, Chapter 5, "Immunoassay Design And Optimization".

*Principles And Practice Of Immunoassay*, Chapter 13, "Heterogeneous Fluoroimmunoassay."

Sambrook et al. *Molecular Cloning: A laboratory manual* (1992) $2^{nd}$ ed. Lake Press, NY.

Service, R. "Radio tags speed compound synthesis" *Science*, (Oct. 27, 1995) vol. 270, p. 577.

Sproat, BS and DM Brown "A new linkage for solid phase synthesis of oligodeoxyribonucleotides" *Nucleic Acids Research* (1985) vol. 13, pp. 2979–2987.

Urdea et al. "A comparison of non–radioisotopic hybridization assay methods using fluorescent, chemiluminescent and enzyme labeled synthetic oligodeoxyribonucleotide probes" *Nucleic Acids Research*, (1988) vol. 16, No. 11 pp. 4937–4956.

* cited by examiner

ELECTRONICALLY-INDEXED SOLID-PHASE ASSAY FOR BIOMOLECULES

This application is a continuation of U.S. Ser. No. 09/163,823 filed Sep. 30, 1998, now abandoned, U.S. Ser. No. 09/163,823 is a continuation of U.S. Ser. No. 08/880,489 filed Jun. 23, 1997, now abandoned, which is a continuation of U.S. Ser. No. 08/565,007 filed Nov. 30, 1995, now U.S. Pat. No. 5,641,634.

BACKGROUND OF THE INVENTION

This invention relates to materials and methods for detecting biomolecules in samples, and more particularly to a particulate solid phase having for encoding information concerning the assay, and to assays employing such a solid phase.

Solid phase assays have been used to determine the presence and/or the concentration of biomolecules, such as proteins, peptides, nucleic acids, carbohydrates and lipids. Solid-phase assays can be performed in a variety of fluids, e.g., simple buffers, biological fluids, such as blood, serum, plasma, saliva, urine, tissue homogenates, and many others.

In solid phase assays, small beads, or microparticles, are typically used as the solid phase to capture the analyte. Solid phase microparticles can be made of a variety of materials, such as glass, plastic or latex, depending on the particular application. Some solid phase particles are made of ferromagnetic materials to facilitate their separation from complex suspensions or mixtures.

In conventional solid-phase assays, the solid phase mainly aids in separating biomolecules that bind to the solid phase from molecules that do not bind to the solid phase. Separation can be facilitated by gravity, centrifugation, filtration, magnetism, immobilization of molecules onto the surface of the vessel, etc. The separation may be performed either in a single step in the assay or, more often, in multiple steps.

Often, it is desirable to perform two or more different assays on the same sample, in a single vessel and at about the same time. Such assays are known in the art as multiplex assays. Multiplex assays are performed to determine simultaneously the presence or concentration of more than one molecule in the sample being analyzed, or alternatively, to evaluate several characteristics of a single molecule, such as, the presence of several epitopes on a single protein molecule.

One problem with conventional multiplex assays is that they typically cannot detect more than about five analytes simultaneously, because of difficulties with simultaneous detection and differentiation of more than about five analytes. In other words, the number of different analytes that may be assayed simultaneously is limited by the solid phase.

SUMMARY OF THE INVENTION

This invention overcomes many of these problems by the use of transponders associated with the solid phase beads to index the particles constituting the solid phase. Thus, each individual transponder-containing solid phase particle can be assigned a unique index number, electronically encoded inside the particle, that can be retrieved by the scanner device at any time, e.g., at one time during the assay, at multiple times during the assay, or continuously during the assay. The index number may relate to the time and date on which the assay was performed, the patient's name, a code identifying the type of the assay, catalog numbers of reagents used in the assay, or data describing the progress of the assay, such as temperature during different steps of the assay.

In an electronically indexed multiplex assay of this invention, two or more transponders, each encoded with a different index number and constructed to bind a different analyte, are incubated with the sample in a single vessel. After necessary additions, incubations and washes are performed, which are similar to incubations and washes in existing assays, the solid phase is analyzed to detect a label indicative of binding of the analyte to the solid phase, such as fluorescence, color, radioactivity or the like. Solid phase analysis is either preceded or followed by the decoding of the index number on the transponder.

Determination of the label and decoding of the memory of the transponder can be done manually on two different instruments, such as a fluorometer and a dedicated scanner, although a single automated instrument that would perform both functions may be used. Such an instrument can be a modified fluorometer in which the scanner is mounted in the proximity of the fluorometer readout window, and reading the sample fluorescence and decoding the transponder are coordinated by a central computer. In addition, such an instrument can be equipped with an automated transport system for transponders.

In one aspect, the present invention provides an electronically-indexed solid phase particle for use in solid phase assays for biomolecules, comprising a transponder and a member of a biomolecular binding pair attached to the transponder.

In another aspect, the present invention provides a method of detecting biomolecules in a sample using solid phase particles having transponders.

In another aspect, the present invention includes a kit for detecting biomolecules in a sample using transponders, comprising assay vessels, a probe reagent, and a labelled conjugate reagent.

DETAILED DESCRIPTION OF THE INVENTION

Figure 1:
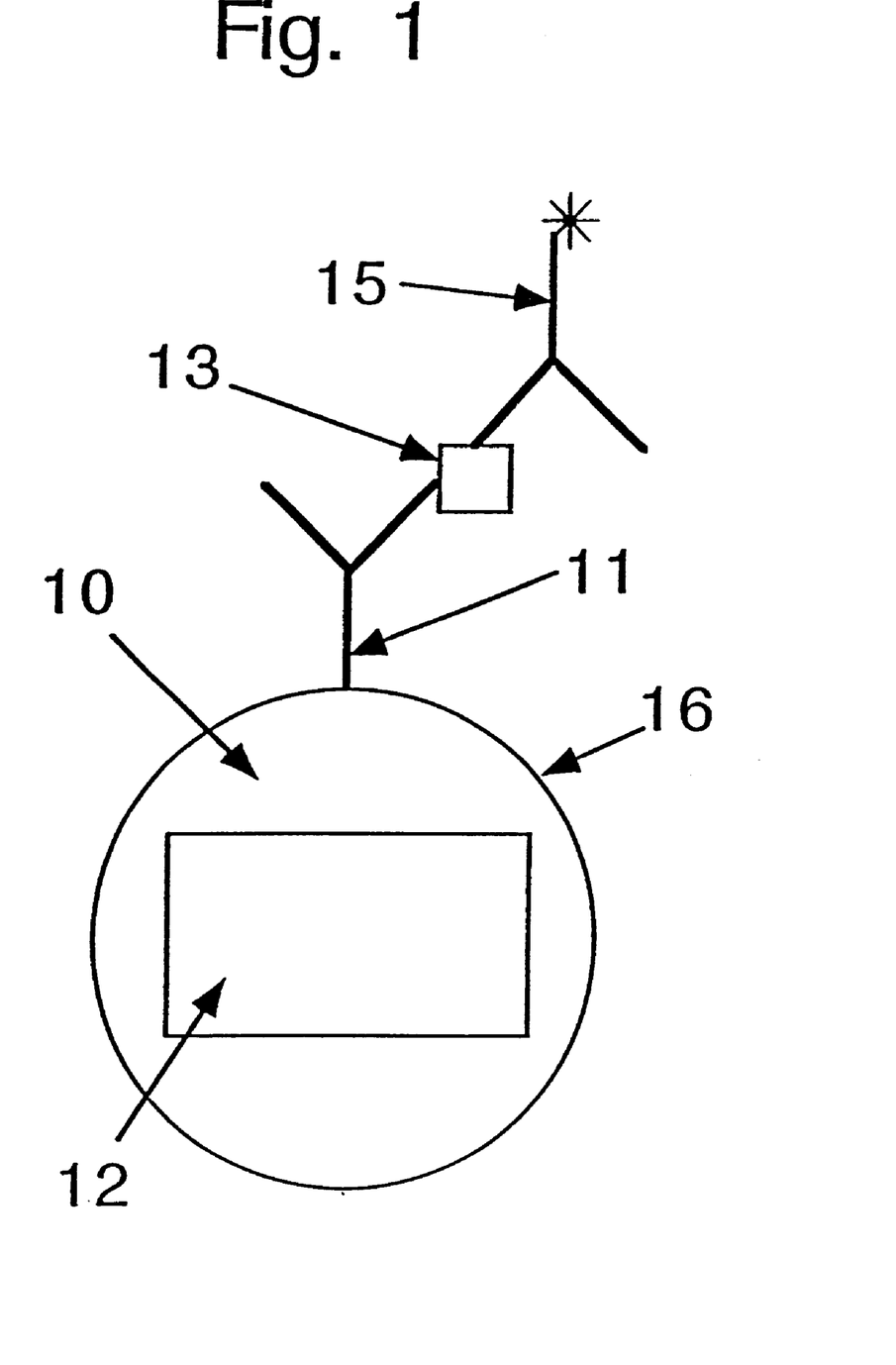
FIG. 1 is a schematic representation of a simple assay of this invention.

FIG. 1 depicts a simple assay of the invention. A solid phase particle 10, with a transponder 12 is derivatized by attaching an antibody 11 to the outer surface 16 of the particle 10. Information concerning the assay, e.g., the assay lot number, is encoded on the transponder, either by the manufacturer of the transponder, or by the user with a remote read/write scanner device (not shown). The derivatized particle 10 is incubated with a sample. Antigen 13 present in the sample is bound by the antibody 11 attached to the particle 10. A second, fluorescent-labelled antibody 15 that binds to the antigen 13 is added to the sample mixture, and the particle 10 is thoroughly washed to remove unbound components. The labelled antibody 15 is detected with a fluorometer to identify those transponders 12 that have antigen 13 bound thereto, and the transponder 12 is decoded using the scanner device (not shown) to retrieve the information encoded thereon. The detection and decoding steps may be done separately or may be done simultaneously. Alternatively, the beads may be pooled into a vessel in no particular order with mixing allowed, and passed through a reader (not shown) that determines and records the fluorescence and, at the same time, decodes the lot number recorded in the transponder 12. It is important to note that when encoding or reading data on a transponder, other transponders must be shielded by a metal barrier, or other means to prevent the electromagnetic radiation from reaching transponders other than the specific target.

Figure 2:
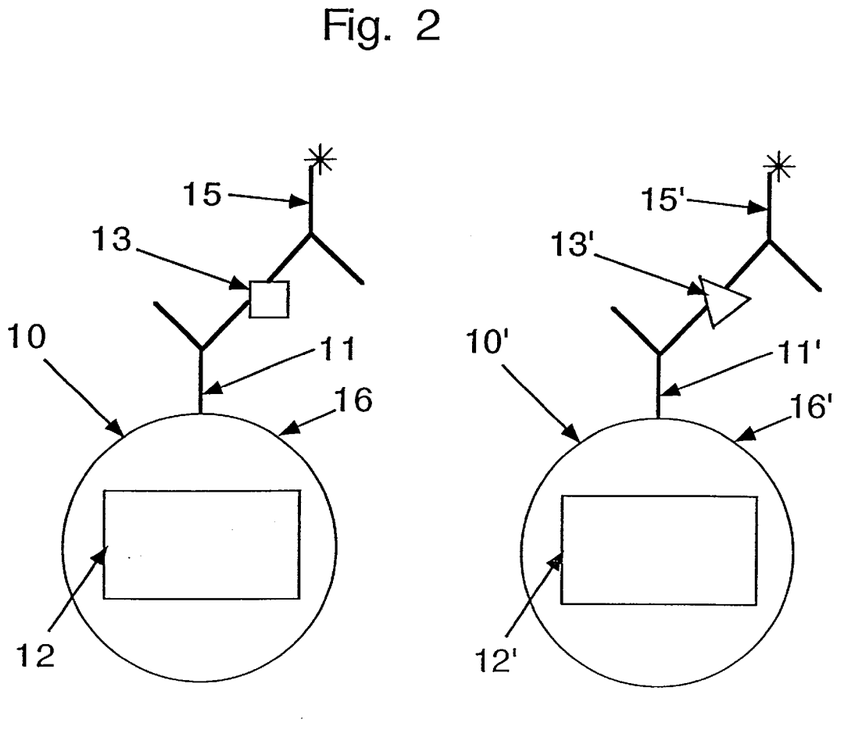
FIG. 2 is a schematic representation of a multiplex assay of this invention.

A multiplex assay according to this invention is conducted in a similar manner, as depicted in FIG. 2, with two or more transponders 12 in each assay vessel (not shown) to detect more than one analyte simultaneously. The transponders 12 are divided into two or more classes 12 and 12', each class having a distinct index number identifying the class, and each class having different antibody 11 and 11' bound to the surface 16 of the particle 10 and 10'. Each class of transponder 12, 12' is separately encoded, either by the manufacturer or by the user with a read/write scanner device (not shown), with an index number to identify, e.g., the antibody 11 bound to the surface 16 of the particle 10. Again, it is necessary to shield other, non-target transponders during the encoding process. The transponders 12, 12' are incubated in the sample vessel and antigen 13, 13' binds to the respective antibody 11, 11'. Second fluorescent-labelled antibodies 15, 15' that bind to the antigens 13, 13' are added to the sample vessel to bind to the antigens 13, 13'. The transponders 12, 12' are then washed thoroughly to remove unbound sample components and reagents. The labelled antibody 15, 15' is detected with a fluorometer to identify those transponders 12, 12' that have antigen 13, 13' bound thereto, and the transponders 12, 12' are decoded using the scanner device (not shown) to retrieve the information encoded thereon. The detection and decoding steps may be done separately or may be done simultaneously. Alternatively, the particles 10, 10' may be pooled into a vessel in no particular order with mixing allowed, and passed through a reader (not shown) that determines and records the fluorescence and, at the same time, decodes the index number recorded in the transponder 12, 12'.

The assays of the present invention may be used with a variety of analytes, including covalently modified proteins and peptides, protein or peptide conjugates, small molecules, ribonucleic acid (RNA), modified nucleic acids and analogs of nucleic acids (in particular protein-nucleic acids, PNAs). The analyte may be a complex of biomolecules, such as a virus particle, a protein-nucleic acid complex, or a protein-hapten complex. The analyte may be a cell, and in such case the relevant molecules that participate in the binding process during the assay are typically cell surface receptors or other elements of the cell wall or membrane. Likewise, the sample may be presented in a variety of forms, such as a solution in a simple buffer, or a complex biological fluid, such as blood, serum, urine, saliva, and many others, or it can be mixed with many other analytes which are simultaneously being assayed for in the multiplex format.

The biomolecules deposited as a primary layer on the surface of the transponder may take a variety of forms, as well, such as covalently modified proteins and peptides, protein or peptide conjugates, small molecules (haptens), ribonucleic acid (RNA), modified nucleic acids and analogs of nucleic acids (in particular protein-nucleic acids, PNAs). The biomolecules can be made in vivo, or in an enzymatic reaction in vitro, or chemically synthesized, either directly or through combinatorial synthesis, or may be a fragment of any of the above products. The purity of the biomolecules deposited as a primary layer on the surface of the transponder can vary as well, from unpurified, partially purified to pure compounds. The biomolecules, their complexes and aggregates, including subcellular structures or cells, can be deposited as a primary layer on the surface of the transponder by a variety of means including, for example, chemical conjugation to an active group on the support, direct chemical synthesis, adhesion or non-specific binding through hydrophobic interactions.

Figure 3:
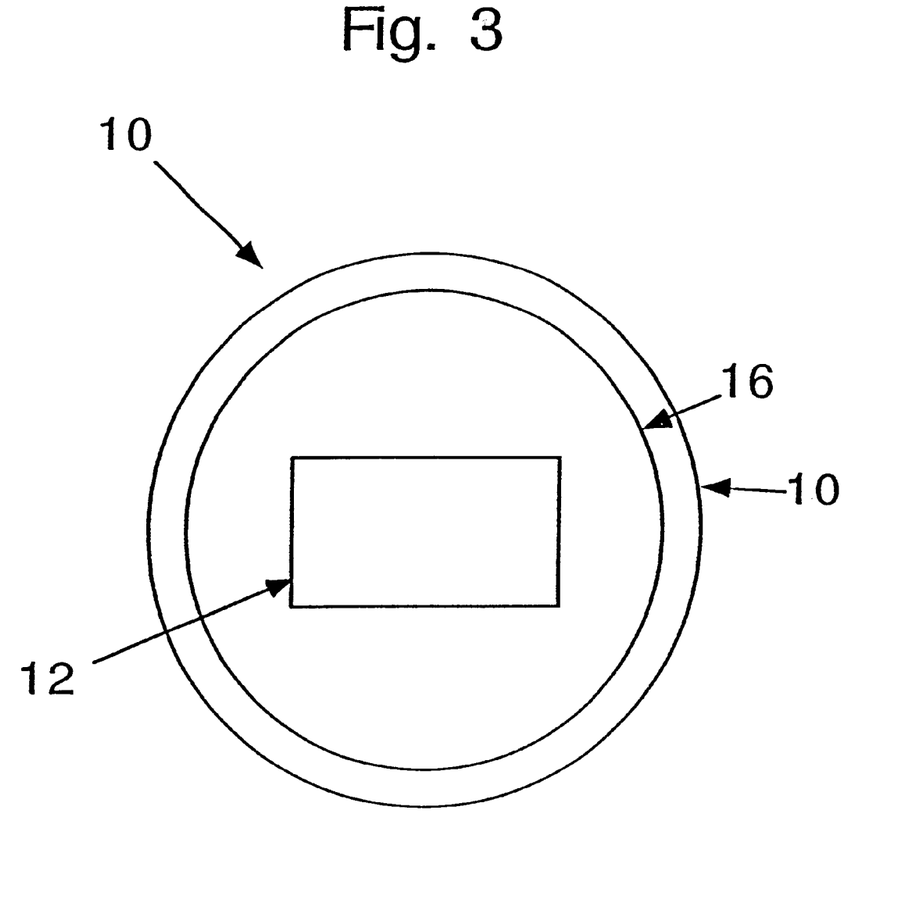
FIG. 3 is a cross-sectional view of a solid phase particle with a transponder and a primary layer of biomolecules bound to a surface thereof.

FIG. 3 depicts a solid phase particle 10 for use in the present inventive methods. The solid phase particle 10 comprises a glass bead with a transponder 12 associated with it, and a member of a biomolecular binding pair (e.g., an antibody or an antigen) attached to the surface 16 of the particle 10 as a primary layer 14. The glass surface 16 of the beads is derivatized through aminoalkylsilane treatment and addition of a cross-linker, to provide primary amine groups on a solid support for further derivatization. The transponder 12 is equipped with a memory element.

A transponder is a radio transmitter-receiver activated for transmission of data by reception of a predetermined signal and may also be referred to as a microtransponder, a radio transponder, a radio tag, etc. The signal comes from a dedicated scanner that also receives and processes the data sent by the transponder in response to the signal. The scanner function can be combined with the write function, i.e., the process of encoding the data on the transponder. Such a combination instrument is referred to as a scanner read/write device. An advantage of the transponder-scanner system is that the two units are not electrically connected by wire, but are coupled inductively, i.e., by the use of electromagnetic radiation, typically in the range from 5–1,000 Khz, but also up to 1 GHz and higher.

Figure 4:
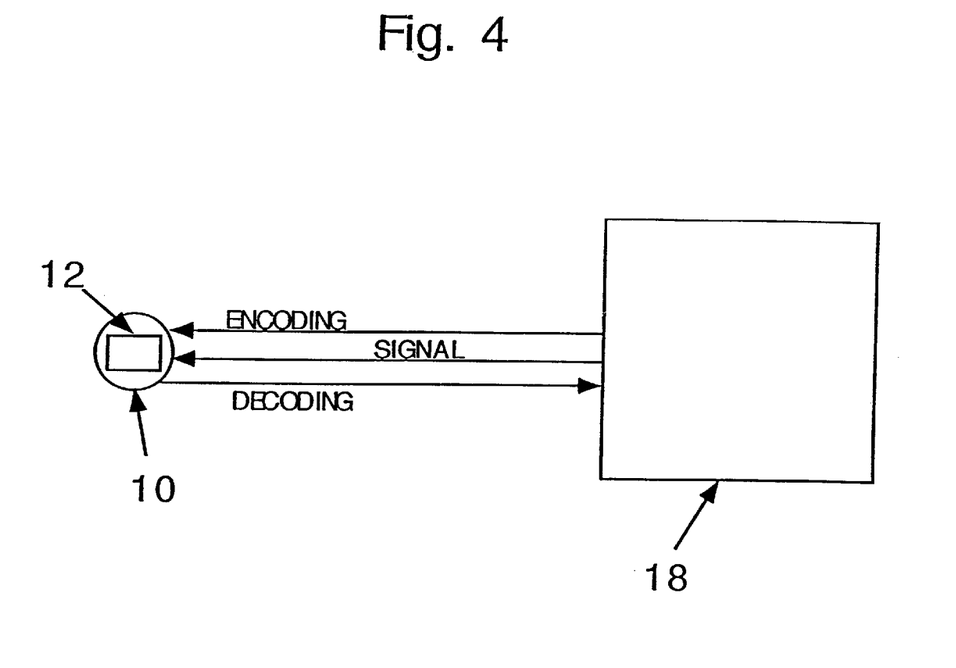
FIG. 4 is a schematic diagram of the signal pathway for encoding and decoding data on the transponders.

FIG. 4 is a flow chart illustrating the communication between the transponder 12 and a remote scanner read/write device 18. The transponder 12 is encoded with data sent by electromagnetic waves from a remote scanner read/write device 18, unless the transponder 12 was pre-encoded by the manufacturer. After the assay steps are completed, the beads 10 are analyzed to detect the presence of a label indicative of binding of analyte and the transponders 12 are decoded. The scanner 18 sends a signal to the transponder 12. In response to the signal, the transponder 12 transmits the encoded data to the scanner 18.

Some transponders similar to the type employed in the present invention are available commercially. For example, BioMedic Data Systems Inc. (BMDS, 255 West Spring Valley Ave., Maywood, N.J.) manufactures a programmable transponder for use in laboratory animal identification. The transponder is implanted in the body of an animal, such as a mouse. The transponder is glass-encapsulated to protect the electronics inside the transponder from the environment. One of the types of transponders manufactured by this corporation, model IPTT-100, has dimensions of 14×2.2×2.2 mm and weighs 120 mg. The transponder is user-programmable with up to 16 alphanumeric characters, the 16th letter programmable independently of the other 15 letters. It has a built-in temperature sensor as well. The electronic animal monitoring system (ELAMS) includes also a scanner read/write system, such as the DAS-5001 console system, to encode or read data on/from the transponder. The construction of the transponder and scanner is described in U.S. Pat. Nos. 5,250,944, 5,252,962, and 5,262,772, the disclosures of which are incorporated herein by reference. Other similar transponder-scanner systems include multi-memory electronic identification tag (U.S. Pat. No. 5,257,011) by AVID Corporation (Norco, Calif.) and a system made by TEMIC-Telefunken (Eching, Germany). AVID's transponder has dimensions of 1 mm×1 mm×11 mm, and can encode 96 bits of information.

The commercially-available transponders are relatively large in size. The speed at which the transponders may be decoded is limited by the carrier frequency and the method of transmitting the data. In typical signal transmission schemes, the data are encoded by modulating either the amplitude, frequency or phase of the carrier. Depending on the modulation method chosen, compression schemes, transmission environment, noise and other factors, the rate of the signal transmission is within two orders of magnitude of the carrier frequency. For example, a carrier frequency of 1,000 Hz corresponds to rates of 10 to 100,000 bits per second (bps). At the rate of 10,000 bps the transmission of 100 bits will take 0.01 sec. The carrier frequency can be several orders of magnitude higher than 1,000 Hz, so the transmission rates can be proportionally higher as well.

Therefore, the limiting factor in the screening process is the speed at which the transport mechanism carries the transponders through the read window of the fluorometer/scanner device. In state-of-the-art flow cytometers, the rate of movement of small particles or cells is $10^4$–$10^5$ per second. A flow cytometer may be used to practice the present invention, if two conditions are met: (1) the transponders are small enough to pass through the flow chamber, and (2) the design of the flow chamber of the flow cytometer is modified to include an antenna and scanner for collecting the electromagnetic radiation emitted by transponders.

Figure 5:
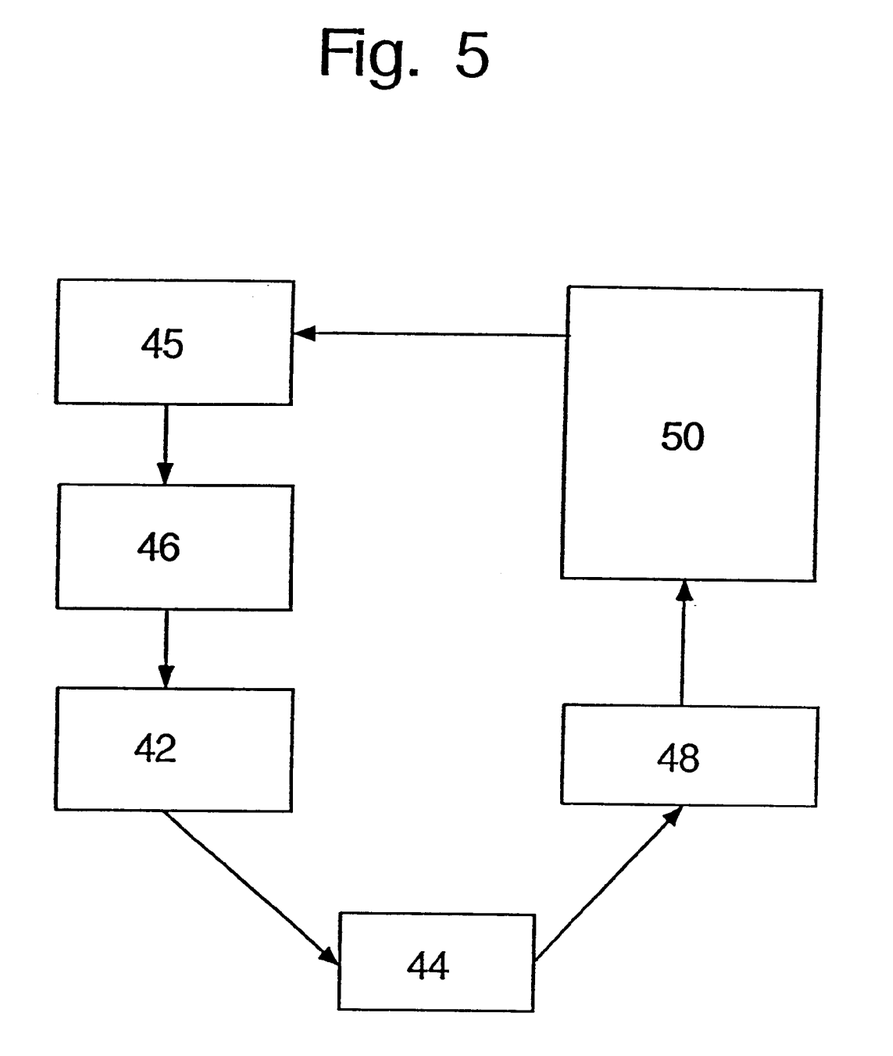
FIG. 5 is a schematic representation of a miniature transponder.
Figure 6:
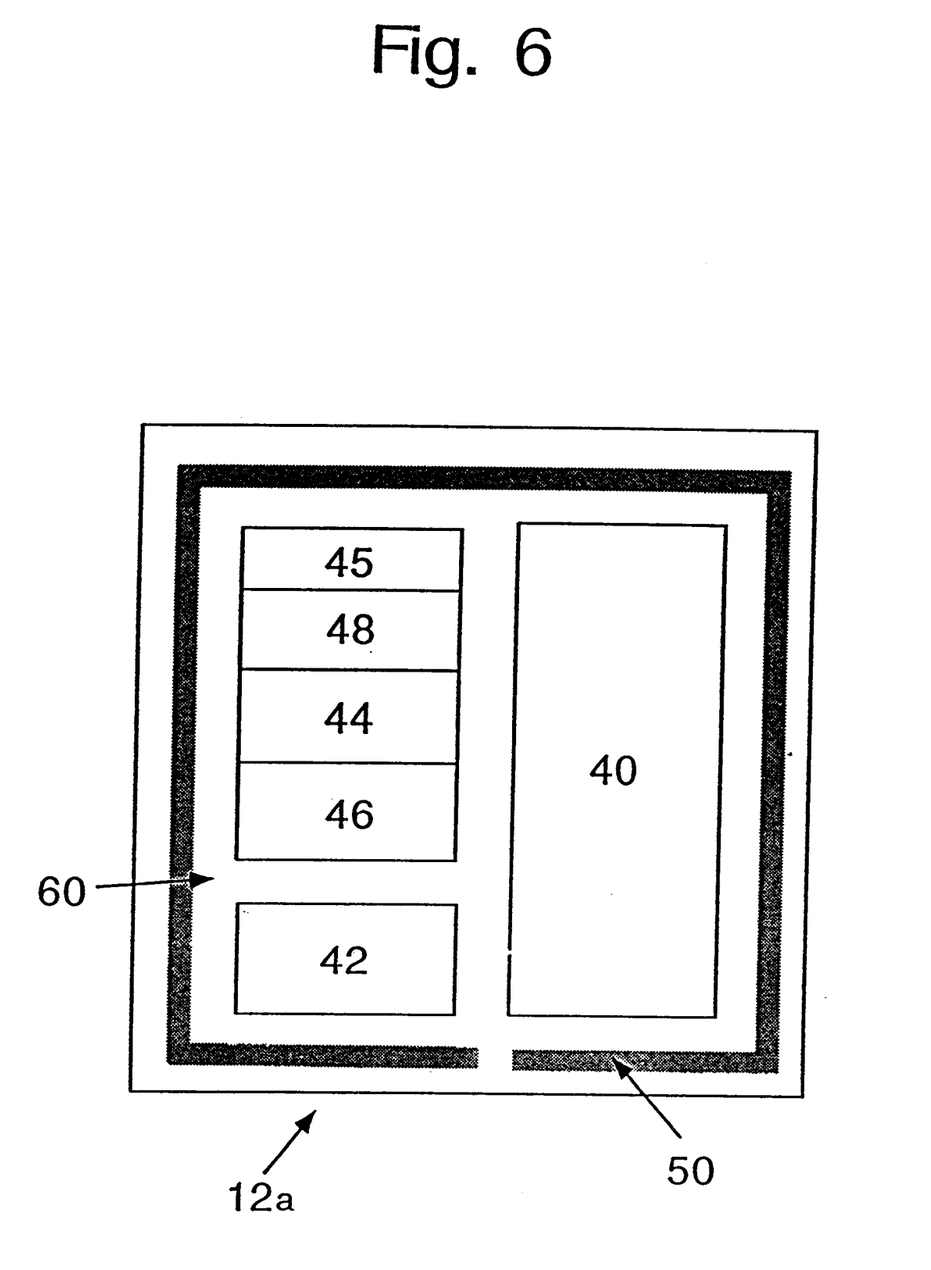
FIG. 6 is a plan view of a miniature transponder.

A miniature transponder is depicted in FIGS. 5 and 6. The source of the electrical power for the transponder 12a is at least one photovoltaic cell 40 within the transponder 12a, illuminated by light, preferably from a laser (not shown). The same light beam induces the fluorescence of fluorogenic molecules immobilized on the surface of the transponder 12a. The transponder 12a includes a memory element 42 that may be of the EEPROM type. The contents of the memory is converted from the digital form to the analog form by a Digital-to-Analog converter 44 mounted on the transponder 12a. The signal is amplified by an amplifier 45, mixed with the carrier signal produced by an oscillator 48, and conducted to the outside of the transponder 12a by an antenna 50.

The contents of memory of the miniature transponder can be permanently encoded, e.g., as ROM memory, during the manufacturing process of the transponder, different batches of transponders being differently encoded. Preferably, the memory of the transponder is user-programmable, and is encoded by the user just before, during, or just after the biological material is deposited on the surface of the transponder. A user-programmable transponder 12a must have the "write" feature enabled by the antenna 50, amplifier 44 and the Analog-to-Digital converter 46 manufactured on the transponder 12a, as well as the dedicated scanner/write device 27.

In a preferred embodiment, the signal from the scanner is transmitted by modulating the intensity of the light illuminating the transponder 12a, which also actuates the photovoltaic cell power source 40.

The advantages of the miniature transponder of FIGS. 5 and 6 are several-fold. First, the transponder dimensions are reduced relative to a conventional transponder, because most of the volume of a conventional transponder is occupied by the solenoid. The current design will enable the production of cubic transponders on the order of 0.01 to 1.0 mm, as measured along a side of the cube, and preferably 0.05 to 0.2 mm.

Second, a large number of transponders can be manufactured on a single silicon wafer. As depicted schematically in FIG. 6, a silicon wafer 60 is simply cut to yield active transponders 12a. Third, the transponder, according the new design, will not need the glass capsule as an enclosure, further reducing the size of the transponder. Silicone dioxide ($SiO_2$) would constitute a significant portion of the surface of the transponder, and $SiO_2$ has chemical properties like glass that allow derivatization or immobilization of biomolecules. Alternatively, microtransponders may be coated with a variety of materials, including plastic, latex, and the like.

Finally, most importantly, the narrow focus of the beam of the laser light would enable only one transponder to be active at a time during decoding, significantly reducing noise level. Advanced user-programmability is desirable as well and, preferably, various memory registers are addressable independently, i.e., writing in one register does not erase the contents of other registers.

Figure 7:
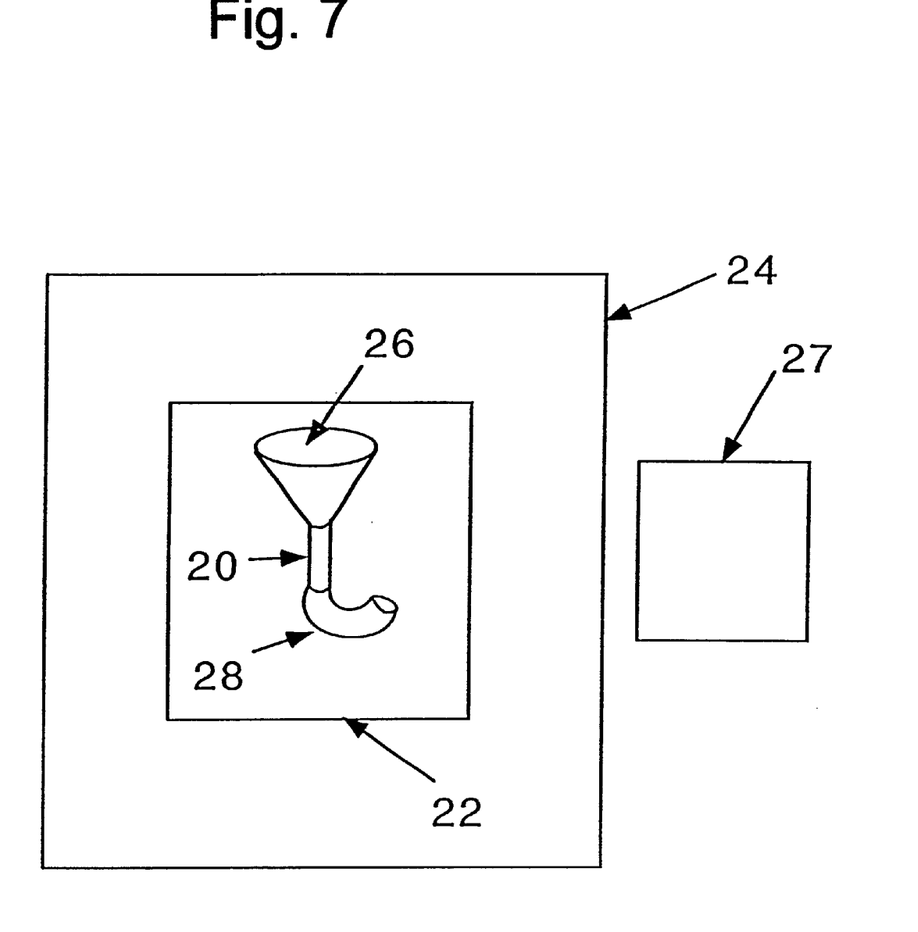
FIG. 7 is a plan view of a transport system/analytical instrument for implementing the present invention.

FIG. 7 shows the analytical instrumentation and transport system used in an embodiment of the present invention. A quartz tube 20 is mounted in the readout window 22 of a fluorometer 24. The quartz tube 20 is connected to a metal funnel 26. The length of the quartz tube 20 is similar to the dimensions of the transponder 12. Transponders 12 are fed into the metal funnel 26, and pass from the funnel 26 into the quartz tube 20, where the fluorescence is read by the fluorometer 24 and the transponder 12 is decoded by the scanner 27, and then exit through a metal tube 28 and are conducted to a collection vessel (not shown). The metal funnel 26 and metal tube 28 are made of metal shield transponders 12 outside of the read window 22 by shielding from the electromagnetic signal from the scanner 27. This shielding prevents the scanner signal from reaching more than one transponder 12, causing multiple transponders 12 to be decoded.

Minimal modification of the fluorometer 24 would be needed in the vicinity of the location that the tube occupies at the readout moment to allow for positioning of the transponder reading device. To assure compatibility with existing assays, the glass surrounding the transponder could be coated or replaced with the type of plastic currently used to manufacture beads.

Figure 8:
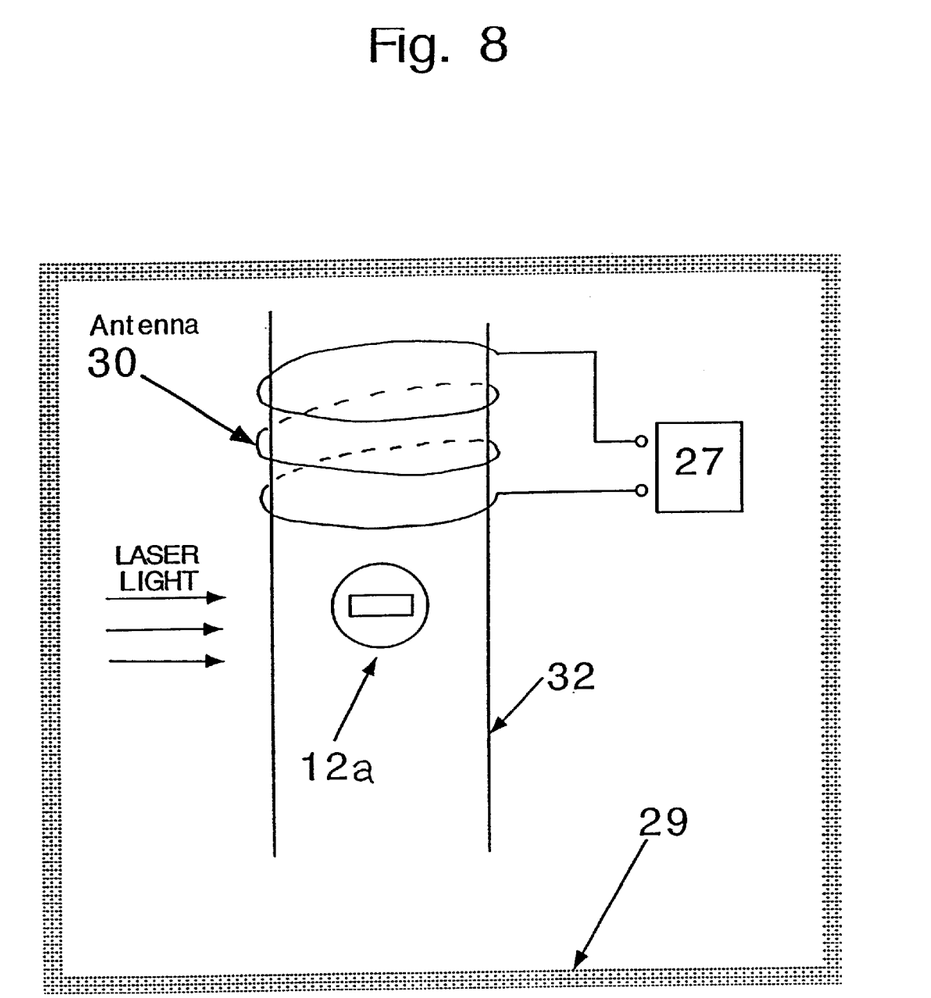
FIG. 8 is a plan view of a modified flow cytometer for high speed analysis of solid phase particles of the present invention.

In a preferred design, depicted in FIG. 8, a modified flow cytometer is used with the miniature transponder of the present invention. A metal coil antenna 30 is wrapped around the flow cell 32 of a flow cytometer 29. The transponders 12a pass through the flow cell 32, and are decoded by the scanner device 27. The signal carrying the data sent from the transponders 12 is amplified by an amplifier 34 and processed by the scanning device 27. As the transponders 12a are decoded, fluorescence from the transponders 12a is detected and analyzed by the flow cytometer 29.

The examples below illustrate various aspects of this invention.

EXAMPLE 1

Preparation of Derivatized Glass Beads Having Transponders

The outside glass surface of transponders (e.g., manufactured by BMDS) is derivatized in the following process.

1. Aminoalkylsilane Treatment

First, the transponders are cleaned by washing with xylene, followed by a 70% ethanol rinse and air drying. Then, the transponders are submerged for about 30 seconds in a 2% solution of aminopropyltriethoxysilane (Cat.# A3648, Sigma, St. Louis, Mo.) in dry acetone. The glass beads are then sequentially rinsed with dry acetone and distilled water, and then air dried. This procedure is described in Pierce catalog (pp. T314–T315 of the 1994 catalog, Pierce, Rockford, Ill.).

2. Attachment of a Linker to Aminoalkylsilane-treated Glass

The aminoalkylsilane-treated transponders are immersed in a 10 mM solution of a homobifunctional NHS-ester cross-linker, $BS^3$, bis(sulfosuccinimidyl)suberate (Pierce Cat.# 21579, described on p. T159 of the 1994 Pierce catalog) in 100 mM phosphate buffer (pH 7.0–7.4) for 5 to 60 minutes at room temperature. The exact incubation time is optimized for each treatment. The transponders are then rinsed with water, submerged in a 10–100 $\mu$M protein solution in 100 mM phosphate buffer (pH 7.4–8.0), and incubated at room temperature for 2–3 hours. The transponders are rinsed three times with 100 mM phosphate buffer (pH 7.4–8.0). The unreacted sites on the glass are blocked by incubating in Blocker BLOTTO in phosphate-buffered saline (PBS, Pierce, Cat.# 37526) for 2 hrs. The transponders are rinsed three times with 100 mM phosphate buffer (pH 7.4–8.0), and stored in this buffer at 4° C.

The described procedure, found in Enzyme Immunodiagnostics, E. Kurstak, Academic Press, New York, 1986, pp. 13–22, works with many proteins. However, since properties of proteins can differ widely, for some proteins alternative immobilization schemes may have to be used.

EXAMPLE 2

Single Assay for a Protein Analyte

The purpose of this assay is to obtain a qualitative indication of the presence of human chorionic gonadotropin (hCG) in the sample, which in this example is a solution of hCG labeled with fluorescein in PBS buffer. Another purpose is to be able to retrieve during the course of the assay the identification of the source of hCG used to prepare the sample.

The surface of the transponder (model IPTT-100, manufactured by BMDS) is derivatized as in Example 1 by aminoalkylsilane treatment, and the $BS^3$ linker is attached to the aminoalkylsilane treated glass. A monoclonal antibody raised against hCG is then conjugated to the linker to form an embodiment of the solid phase particle of the present invention.

A transponder derivatized with the anti-hCG antibody is immersed in 1 ml of PBS in a test tube. A fluorescein-labeled HCG preparation is added to the test tube. The final concentration is between 50 pg/ml and 50 $\mu$g/ml. The transponder is incubated at room temperature for 30 minutes. During that time, six alphanumeric characters constituting the sample lot-number identifying the source of hCG is encoded into the memory of the transponder using a dedicated read/write scanner. Additional information such as the lot number of the antibody preparation used, or the name of the patient who donated the serum containing hCG may also be encoded on the transponder. After a series of extensive washes over a period of 5 minutes, the transponder is placed in 1 ml of fresh PBS buffer. The transponder is then placed in a fluorometer, and the fluorescence intensity (FI) is measured and recorded. The FI readout is normalized with respect to positive control transponders which were exposed to fluoresceinated bovine serum albumin instead of fluoresceinated hCG. The electronic memory of the transponder is decoded using a dedicated scanner to obtain the lot number of the hCG preparation.

The advantage of using the transponder in this example instead of a prior art solid phase particle is that there is no need to maintain an association between the test tube and the solid phase at all times during the assay. Instead, after electronically recording the lot number, the transponder can be separated from the original container without losing track of the lot number of the sample to which it was exposed. The transponder can be mixed with other transponders exposed to analytes having different lot numbers without losing information about the presence of hCG in the analyte.

EXAMPLE 3

Electronically Indexed Solid Phase Assay for Human IgA1 AND IgG1

A total of eight transponders (e.g., BMDS model IPTT-100) are derivatized according to the procedure of Example 1, with two antibodies, human IgA1 (Cat.# I2636) and IgG1 (Cat.# I4014) obtained from Sigma (St. Louis, Mo.). Thus, two groups of transponders carrying these two antibodies are obtained. Four transponders of each of the two groups of transponders are encoded with the index numbers A1, A2, A3 and A4, and G1, G2, G3 and G4, respectively, by the read/write scanner device (BMDS). The letter corresponds to the type of immunoglobulin used to derivatize the transponder, and the digit gives the tube number. Transponders are distributed into assay tubes, each tube containing one transponder of each type. Thus, tube 1 contains transponders encoded A1 and G1, tube 2-A2 and G2, etc.

The following set of analytes is prepared at a concentration between 50 pg/ml and 50 $\mu$g/ml in PBS:

Analyte 1: Mixture of monoclonal antibody to human IgA1 labeled with FITC (Cat.#F6016), and monoclonal antibody to human IgG1 labeled with FITC (Cat.#F5016).

Analyte 2: Monoclonal antibody to human IgA1 labeled with FITC.

Analyte 3: Monoclonal antibody to human IgG1 labeled with FITC.

Analyte 4: No antibody present.

2 mls of analyte 1 is added to tube 1, containing two transponders, one of each group as described above. Similarly, 2 mls of analyte 2, 3 and 4 are added to tubes 2, 3 and 4, respectively, also containing two transponders each. The tubes are kept at room temperature for 30 minutes, after which the transponders are washed three times with 5 ml PBS buffer. The fluorescence of each of the transponders is quantitated by using a FluorImager (Molecular Dynamics), and the encoding of each transponder is determined by using the read/write device (BMDS).

The assay described is direct, since the concentration of FITC-derivatized antibody is measured. Alternatively, the assay can be configured in a competitive format to measure the concentration of underivatized antibodies, such as those present in sera. Moreover, the number of analytes that can be tested in one tube is limited only by the requirement that the total volume of the transponders needed in the single tube should not be much larger than the sample volume.

EXAMPLE 4

Multiplex Assay for Antibodies Employing Peptides Immobilized on Transponders Peptides can be immobilized on the surface of the transponders' glass envelope by either chemical synthesis or conjugation. The glass surface of the transponder (e.g., AVID) is first derivatized with aminopropyltriethoxysilane, creating a suitable solid support for chemical peptide synthesis. The amino groups of the alkyl chains attached to the support are appropriate for initiating peptide synthesis by forming the amide bond with the C-terminal residue of the peptide when standard Fmoc or Boc chemistries are used. The resulting peptide can be deprotected according to standard protocols without cleaving the peptide from the support.

Alternatively, peptides previously synthesized or isolated can be attached to the treated glass surface using the cross-linker and protocol of Example 1. The requirement will be the presence of a primary amine group in the peptide (such as N-terminal amine), or a secondary amine group. The assay configuration is identical to Example 1, except that the proteins (i.e. monoclonal antibodies) of Example 1 are replaced with peptides in this Example.

EXAMPLE 5 a Diagnostic Kit for Performing an Electronically Indexed Multiplex Assay for the Hepatitis C Virus The kit is used to simultaneously determine the presence of antibodies to four Hepatitis C Virus (HCV) antigens in human serum or plasma, or in mixtures of purified anti-HCV antibodies prepared in the laboratory. The HCV antigens are as follows: (1) core, (2) NS3, (3) NS4, N-terminal part, (4) NS4, C-terminal part.

The constituents of the HCV reagent kit are as follows:

1. Reagent A, Specimen Diluent, 10 Mm Tris-HCL, pH 7.5. Preservative: 0.1% sodium azide.
2. Reagent B, Probe. Goat antibody to human IgG (H+L), conjugated to biotin. Minimum concentration; 0.1 pg/ml. Preservative: 0.1% sodium azide.
3. Reagent C, Conjugate. Rabbit antibody to biotin, conjugated to alkaline phosphatase. Minimum concentration: 0.1 pg/ml. Preservative: 0.1% sodium azide.
4. Reagent D, Chromogen. 5-bromo-4-chloro-3 indolyl phosphate (0.1%). Preservative: 0.1% sodium azide.
5. 20 Test Vessels. Each vessel is a 2 ml test tube and contains 4 transponders conjugated to four HCV antigens. The antigens are applied at a minimum of 1 ng per transponder. The transponders are electronically encoded with numbers 1,2,3 and 4, corresponding to antigens (1),(2),(3) and (4) respectively.
6. 1 Vial (0.1 ml) Accessory Positive Control. It is an inactivated human plasma containing antibody to HCV, non-reactive for HBsAg and antibody to HIV-I/HIV-2. Minimum titer: 1:2. Preservative: 0.1% sodium azide.
7. 1 Vial (0.1 ml) Accessory Negative Control. It is human plasma nonreactive by FDA licensed tests for antibody to HCV, and non-reactive for HBsAg and antibody to HIV-l/HIV-2. Preservative: 0.1% sodium azide.
8. Wash buffer. 10 mM Tris-HCL, pH 7.5.
9. Enzyme Reaction Buffer, 100 mM Tris-HCL, pH 8.0.
10. Bar coded calibration data sheet.

In an alternative configuration of the kit, the chromogen, reagent 4 above, is replaced with a fluorogen, item 4a and Reagent 4a, namely:

4a. Reagent 4-a, Fluorogen, precipitating substrate for alkaline phosphatase (0.1%). The substrate is attophos reagent, manufactured by JBL Scientific, San Luis Obispo, Calif. Preservative: 0.1% sodium azide.

The procedure for performing the assay on a single sample of unknown composition with regard to HCV antibodies is as follows. Three test vessels, X, Y and Z are placed in a rack. Sample is added to vessel X, Accessory Positive Control added to vessel Y, Accessory Negative Control added to vessel Z. Appropriate amounts are determined for each lot of reagents, but approximate volumes are 10–100 µl sample or controls diluted with the Wash Buffer to the final volume of 2 ml. The sample and buffer are thoroughly mixed, and incubated for 30 minutes at room temperature, after which the transponders in the vessel are washed extensively for 5 minutes with the Wash Buffer. Reagent B is then added, and the vessel is incubated for 30 minutes, after which the transponders are washed. Reagent C is then added, and the vessel is incubated for 30 minutes, after which the transponders are washed. One ml of the enzyme reaction buffer is then added to the vessels, followed by 1 ml of the substrate (item 4 or 4a). The contents of the vessels is mixed thoroughly. The vessels are incubated at room temperature for 2 to 30 minutes, depending on the desired sensitivity of the assay, after which the transponders are rinsed with the Wash Buffer to remove excess substrate and that fraction of the product of the reaction which did not precipitate. The color of the transponders is then determined in a photodiode spectrophotometer configured to measure the reflected light, or the fluorescence of the transponders is measured in a fluorometer, depending on the label used. Each optical measurement is followed by the decoding of the electronic memory of the transponder and associated with the optical measurement.

What is claimed is:

1. A solid phase for use in fluorescence assays for biomolecules comprising:
    a. a transponder manufactured on a single silicon wafer and comprising of memory elements, a radio-frequency transmitter and one or more photovoltaic cells, and
    b. a first member of a biomolecular binding pair attached directly or indirectly to an outer surface of the transponder,
    wherein,
        i. the memory elements contain an index number identifying the solid phase,
        ii. the photovoltaic cell(s) provide a source of electrical power for the memory elements and transmitter when illuminated by laser light,
        iii. the biomolecular binding pair member specifically binds to the biomolecule,
        iv. the biomolecular binding pair member directly or indirectly binds fluorescently labeled molecules which are detected by measuring fluorescence induced by the laser light, and
        v. the memory elements are decoded by means of illumination with light.

2. The solid phase of claim 1, wherein one or more layers of coating are deposited on the outer surface of the transponder and the first member of a biomolecular binding pair is attached to a coating layer.

3. The solid phase of claim 2, wherein the layers of coating comprise of glass, latex or plastic.

4. The solid phase of claim 1, wherein the first member of a biomolecular binding pair is a member of an antigen-antibody binding pair.

5. The solid phase of claim 1, wherein the first member of a biomolecular binding pair is a nucleic acid.

6. The solid phase of claim 1, wherein the transponder has a volume of less than 10 mm$^3$.

7. The solid phase of claim 1, wherein the transponder has a volume of less than 1 mm$^3$.

8. The solid phase of claim 1, wherein the memory elements are encoded with the index number during manufacture of the transponder.

9. The solid phase of claim 1, wherein the memory elements are encoded with the index number during manufacture of the solid phase.

10. The solid phase of claim 1, wherein the memory elements are encoded with the index number by a user.

* * * * *